United States Patent
Lindquist (10) Patent No.: US 10,500,587 B2
(45) Date of Patent: Dec. 10, 2019

(54) FERRO-MAGNETIC SHAPE MEMORY ALLOY MICROCAVITY FLUID SENSOR

(71) Applicant: BOISE STATE UNIVERSITY, Boise, ID (US)

(72) Inventor: Paul G. Lindquist, Eagle, ID (US)

(73) Assignee: BOISE STATE UNIVERSITY, Boise, ID (US)

( * ) Notice: Subject to any disclaimer, the term of this patent is extended or adjusted under 35 U.S.C. 154(b) by 115 days.

(21) Appl. No.: 15/215,039

(22) Filed: Jul. 20, 2016

(65) Prior Publication Data

US 2018/0021775 A1    Jan. 25, 2018

(51) Int. Cl.
| | | |
|---|---|---|
| B01L 3/00 | (2006.01) | |
| G01N 27/416 | (2006.01) | |
| G01N 21/25 | (2006.01) | |

(52) U.S. Cl.
CPC ..... B01L 3/502715 (2013.01); B01L 3/50273 (2013.01); G01N 21/25 (2013.01); B01L 2300/0645 (2013.01); B01L 2300/0654 (2013.01); B01L 2300/12 (2013.01); B01L 2300/168 (2013.01); B01L 2400/0493 (2013.01); G01N 27/416 (2013.01)

(58) Field of Classification Search
CPC .............. G01N 21/25; G01N 27/416; B01L 3/502715; B01L 3/50273; B01L 2200/0642; B01L 2300/0645; B01L 2300/0654; B01L 2300/12; B01L 2300/168; B01L 2300/0493

See application file for complete search history.

(56) References Cited

U.S. PATENT DOCUMENTS

| | | | |
|---|---|---|---|
| 5,205,819 A | 4/1993 | Ross et al. | |
| 6,100,541 A | * 8/2000 | Nagle | B01L 3/5027 204/603 |
| 6,767,706 B2 | 7/2004 | Quake et al. | |
| 6,916,159 B2 | 7/2005 | Rush et al. | |

(Continued)

OTHER PUBLICATIONS

Smith et al., "Characterization of a high resolution solid state micropump that can be integrated into microfluidic systems", Microfluid Nanofluid, Jan. 8, 2015.*

(Continued)

*Primary Examiner* — Matthew T Martin
(74) *Attorney, Agent, or Firm* — Parsons Behle & Latimer (57) ABSTRACT

A micropump includes a body with an inlet and an outlet defined therein. A channel connects the inlet to the outlet. The micropump further includes a magnetic shape memory (MSM) alloy positioned within the channel. The MSM alloy selectively forms a barrier between the inlet and the outlet. The micropump also includes an electrode and/or a transparent window positioned along a surface of the channel. A cavity is selectively formed within a surface of the MSM alloy due to a magnetic field. The cavity is selectively moveable between a first position adjacent to the inlet, a second position adjacent to the electrode and/or the transparent window, and a third position adjacent to the outlet, by altering the magnetic field. By altering a magnetic field applied to the MSM alloy, a fluid may be pumped from the inlet to the electrode and/or the transparent window where the fluid may be analyzed. The fluid may be subsequently pumped to the outlet.

8 Claims, 5 Drawing Sheets

(56) References Cited

U.S. PATENT DOCUMENTS

| | | |
|---|---|---|
| 6,951,632 B2 | 10/2005 | Unger et al. |
| 7,025,323 B2 | 4/2006 | Krulevitch et al. |
| 7,111,501 B2 | 9/2006 | Rocklin et al. |
| 7,364,647 B2 | 4/2008 | Paul et al. |
| 7,540,717 B2 | 6/2009 | Sheng et al. |
| 7,703,336 B2 | 4/2010 | Genosar |
| 7,708,872 B2 | 5/2010 | Eidsnes et al. |
| 7,718,047 B2 | 5/2010 | Koval et al. |
| 7,794,660 B2 | 9/2010 | Connelly et al. |
| 7,832,429 B2 | 11/2010 | Young et al. |
| 7,976,795 B2 | 7/2011 | Zhou et al. |
| 9,216,412 B2 | 12/2015 | Putnam et al. |
| 2008/0015494 A1 | 1/2008 | Santini, Jr. et al. |
| 2010/0269579 A1 | 10/2010 | Lawrence et al. |
| 2013/0209278 A1 | 8/2013 | Locke et al. |
| 2014/0332410 A1* | 11/2014 | Ben-Yoav .......... G01N 27/3277 205/782 |
| 2014/0356849 A1 | 12/2014 | Wikswo et al. |
| 2015/0267695 A1 | 9/2015 | Marsh |
| 2015/0276588 A1 | 10/2015 | Marshall et al. |
| 2016/0010761 A1 | 1/2016 | Laser et al. |

OTHER PUBLICATIONS

Matos Pires et al., "Recent Developments in Optical Detection Technologies in Lab-on-a-Chip Devices for Biosensing Applications", 2014.*

* cited by examiner

FERRO-MAGNETIC SHAPE MEMORY ALLOY MICROCAVITY FLUID SENSOR

FIELD OF THE DISCLOSURE

This disclosure relates generally to the field of ferro-magnetic shape memory alloy microcavity fluid sensing.

BACKGROUND

Micropumps enable pumping very small quantities (e.g., in the nano or micro liter range) of fluid. Described in U.S. Pat. No. 9,091,251, filed on Jul. 16, 2012, and entitled "Actuation method and apparatus, micropump, and PCR enhancement method," is a micropump design where the active pumping element is a single crystal of a magnetic shape memory (MSM) alloy. The magnetic field, from a rotating cylindrical magnet (magnetized across the diameter of the cylinder), creates a microcavity in the MSM element which is swept from the pump inlet to the outlet. The microcavity fills with fluid at the inlet which is swept by a rotating cylindrical magnet across the MSM element to the outlet where the fluid is pushed out. The pump cycle repeats for every rotation of the magnet. U.S. Pat. No. 9,091,251 is hereby incorporated by reference in its entirety.

Typical micropumps, such as the micropump describe above, do not enable chemical or optical analysis to be performed on a fluid within the microcavity while the fluid is in the pump. Further, typical micropumps continuously pump fluid and do not enable a small sample of fluid to be stopped within the pump for analysis.

SUMMARY

Disclosed herein are embodiments of a micropump that overcome at least some of the shortcomings associated with typical micropumps. In an embodiment, microelectrodes are placed between the inlet and outlet of a micropump such that a fluid within a microcavity of the pump contacts the microelectrodes for each pump cycle. The microelectrodes may enable electrochemical measurements on the fluid flowing through the pump. In this embodiment, the micropump may be similar to Ion Chromatography (IC) systems. Since the displacement of the microcavity is controlled by the rotation of the magnetic field, the microcavity can be stopped near the microelectrodes and the fluid can be analyzed for electrochemical activity (e.g., via a three electrode electrochemical cell). Further, a potentiostat may be used to electrochemically reduce or oxidize the solution in the microcavity, similar to processes used in High Pressure Liquid Chromatography (HPLC) systems.

In an embodiment, a window is placed between the inlet and the outlet. The window may enable optical detection and analysis of a fluid within the pump for each cycle. In this embodiment, an optical detector may be used to count cells or particles as they are pumped through the micropump. The low volume of solution pumped through the micropump (e.g., in the nano-liter or micro-liter range) may enable the counting of the cells or particles. For example, an optical detection system may be trained to identify the cells or particle through the window to quantify the concentration, size and type of cell or particle as they travel within the microcavity.

In an embodiment, a micropump includes a body with an inlet defined within the body and with an outlet defined within the body. The micropump further includes a channel connecting the inlet to the outlet. The micropump also includes an MSM alloy positioned within the channel forming a barrier between the inlet and the outlet. The micropump includes an electrode positioned along a surface of the channel. The micropump further includes a cavity formed within a surface of the MSM alloy due to a magnetic field. The cavity is selectively moveable between a first position adjacent to the inlet, a second position adjacent to the electrode, and a third position adjacent to the outlet, by altering the magnetic field.

In some embodiments, the micropump also includes a second electrode such that the electrode, the second electrode, and the MSM alloy contact a fluid within the cavity when the cavity is in the second position. In some embodiments, the micropump includes a voltage source coupled in series between the electrode and the second electrode to enable application of a voltage potential to the fluid between the electrode and the second electrode. In some embodiments, the micropump further includes a third electrode to enable in contact with the fluid within the cavity when the cavity is in the second position. The third electrode may enable measurement of a common voltage during application of the voltage potential. In some embodiments, the MSM alloy is configured to enable measurement of a common voltage during application of the voltage potential.

In some embodiments, the micropump further includes another electrode positioned along the surface of the channel. The cavity may be further selectively moveable to a position adjacent the other electrode. In some embodiments, the micropump includes additional electrodes positioned along the surface of the channel and the cavity is selectively moveable to the additional positions. In some embodiments, the micropump also includes a transparent window defined within the body and positioned adjacent the channel. The cavity may be selectively moveable to a position adjacent the transparent window. The micropump may include an optical detector directed toward the transparent window. In some embodiments, the micropump includes an activation device configured to activate at least one material identified via the transparent window. The activation device includes at least one of a laser and an electrical pulse source.

In an embodiment, a micropump includes a body, an inlet defined within the body, and an outlet defined within the body. The micropump further includes a channel connecting the inlet to the outlet. The micropump also includes an MSM alloy positioned within the channel forming a barrier between the inlet and the outlet. The micropump includes a transparent window defined within the body and positioned adjacent the channel. The micropump further includes a cavity formed within a surface of the MSM alloy due to a magnetic field. The cavity is selectively moveable between a first position adjacent to the inlet, a second position adjacent to the transparent window, and a third position adjacent to the outlet, by altering the magnetic field.

In some embodiments, the transparent window is transparent to light within a predefined bandwidth. In some embodiments, the micropump further includes a light source directed toward the window. In some embodiments, the micropump also includes a detector directed toward the transparent window. In some embodiments, the micropump includes an activation device configured to activate at least one material identified via the transparent window. The activation device includes at least one of a laser and an electrical pulse source.

In an embodiment, a method includes actuating a micropump to move a cavity formed within a surface of a MSM alloy from a first position adjacent to an inlet, to a second position adjacent to an electrode, a transparent window, or both. The method further includes performing an electro-analysis operation, an optical analysis, or both, on a fluid within the cavity. The method also includes actuating the micropump to move the cavity from the second position to a third position adjacent to an outlet.

In some embodiments, performing the electro-analysis operation includes applying a voltage potential between the electrode and a second electrode in contact with the fluid within the cavity. In some embodiments, performing the electro-analysis operation includes measuring a common voltage via a third electrode in contact with the fluid within the cavity. In some embodiments, performing the electro-analysis operation includes measuring a common voltage via the MSM alloy. In some embodiments, performing the optical analysis includes identifying a concentration of a substance within the fluid based on spectrophotometry. In some embodiments, actuating the micropump includes altering a magnetic field applied to the MSM alloy.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the disclosure as defined by the appended claims.

DETAILED DESCRIPTION

Figure 1:
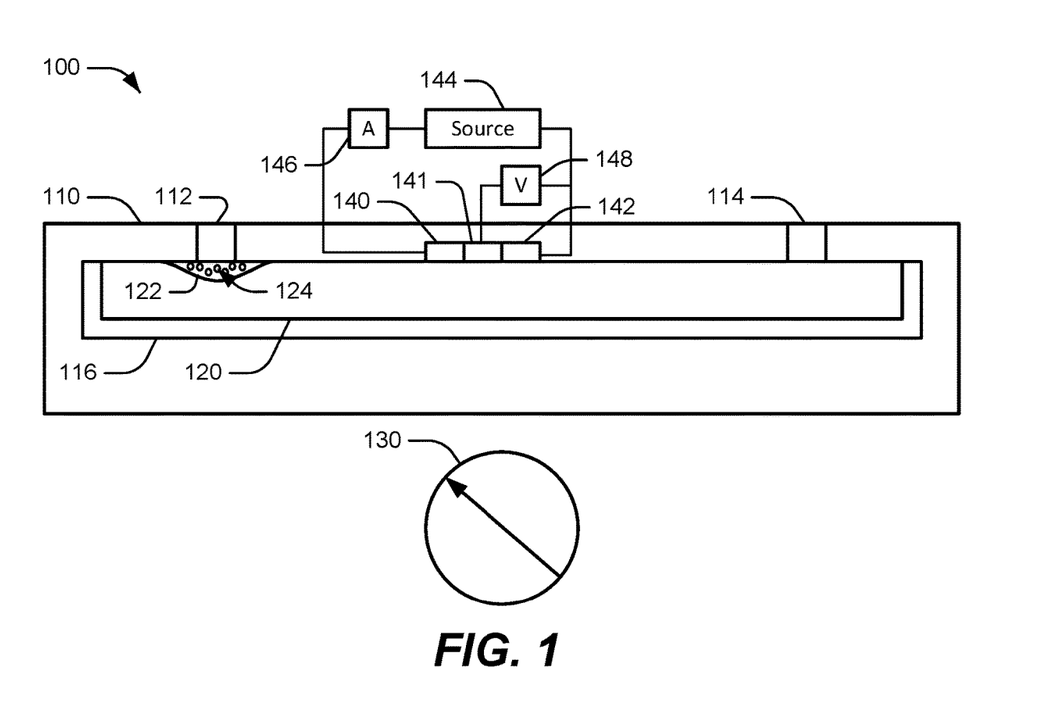
FIG. 1 is a diagram depicting an embodiment of a system for MSM alloy microcavity fluid sensing.

Referring to FIG. 1, an embodiment of a system 100 for MSM alloy microcavity fluid sensing is depicted. The system 100 may include a micropump body 110, a MSM alloy 120, a magnetic field source 130, and a set of electrodes 140-142.

The micropump body 110 may include an inlet 112 and an outlet 114 defined therein. The inlet 112 and the outlet 114 may be connected via a channel, opening, or slot 116 hereafter referred to as a channel through the body 110. The micropump body 110 may be molded or otherwise formed from as a continuous component or may be formed from multiple components coupled together. Further, although the channel 116 is depicted as fully enclosing the MSM alloy 120, in some embodiments the channel 116 only encloses a portion of the MSM alloy 120 sufficient to retain a fluid 124 as described herein.

The MSM alloy 120 may be positioned within the channel 116 to selectively form a barrier between the inlet 112 and the outlet 114. For example, the MSM alloy 120 may be positioned adjacent to an inner surface of the body 110 covering the inlet 112 and the outlet 114 to prevent the fluid 124 from flowing freely between the inlet 112 and the outlet 114. As explained further herein, a cavity 122 may be formed within the MSM alloy 120 to move the fluid 124 from the inlet 112 to the outlet 114, thereby bypassing the barrier formed by the MSM alloy 120. In some embodiments, the MSM alloy 120 has an elongated shape and is positioned along a substantially linear path between the inlet 112 and the outlet 114. Suitable alloys for use as the MSM alloy 120 and its properties are further described with reference to U.S. Pat. No. 9,091,251, incorporated by reference above.

The magnetic field source 130 may be positioned in proximity to the MSM alloy 120. In some embodiments, the magnetic field source may include a permanent magnet or combinations of permanent magnets. An example of a magnetic field source is further described with reference to U.S. Pat. No. 9,091,251, incorporated by reference above. In some embodiments, other types of magnetic field sources may also be used.

The electrodes 140-142 may be configured in a three-electrode chemical cell configuration. For example, the electrodes 140-142 may include a counter electrode 140, a reference electrode 141, and a working electrode 142. A voltage potential source 144 may be coupled in series with the counter electrode and the working electrode. An ammeter 146 may be also be coupled to the circuit between the counter electrode 140 and the working electrode 142. A voltmeter 148 may be coupled between the reference electrode 141 and the working electrode 142. The three-electrode chemical cell configuration may enable the identification of a substance and/or a concentration of a substance within the fluid 124 in contact with each of the electrodes 140-142. In some embodiments, suitable materials for the electrodes 140-142 include copper, platinum, noble metals, or combinations thereof. Although FIG. 1 depicts a three-electrode chemical cell configuration, other configurations and other numbers of electrodes fall within the scope of this disclosure as would be appreciated by one of ordinary skill in the art having the benefit of this disclosure.

During operation, the magnetic field source 130 may be configured to generate a magnetic field that is substantially perpendicular to the MSM alloy 120 within a narrow region along the length of the MSM alloy 120 and that is substantially parallel to the MSM alloy along the rest of the length of the MSM alloy 120. Due to the magnetic field, the MSM alloy 120 may deform within the narrow region to form a cavity 122. A mechanism for forming the cavity 122 within in the MSM alloy 120 is further described with reference to U.S. Pat. No. 9,091,251, incorporated by reference above. For purposes of this disclosure, the arrow within the magnetic field source 130 provides a general indication of where along the MSM alloy 120 the substantially perpendicular magnetic field component is directed. By directing the magnetic field toward the inlet 112, the cavity 122 may be positioned adjacent to the inlet 112. After the cavity 122 is formed and positioned, the fluid 124 may be received therein via the inlet 112.

Figure 2:
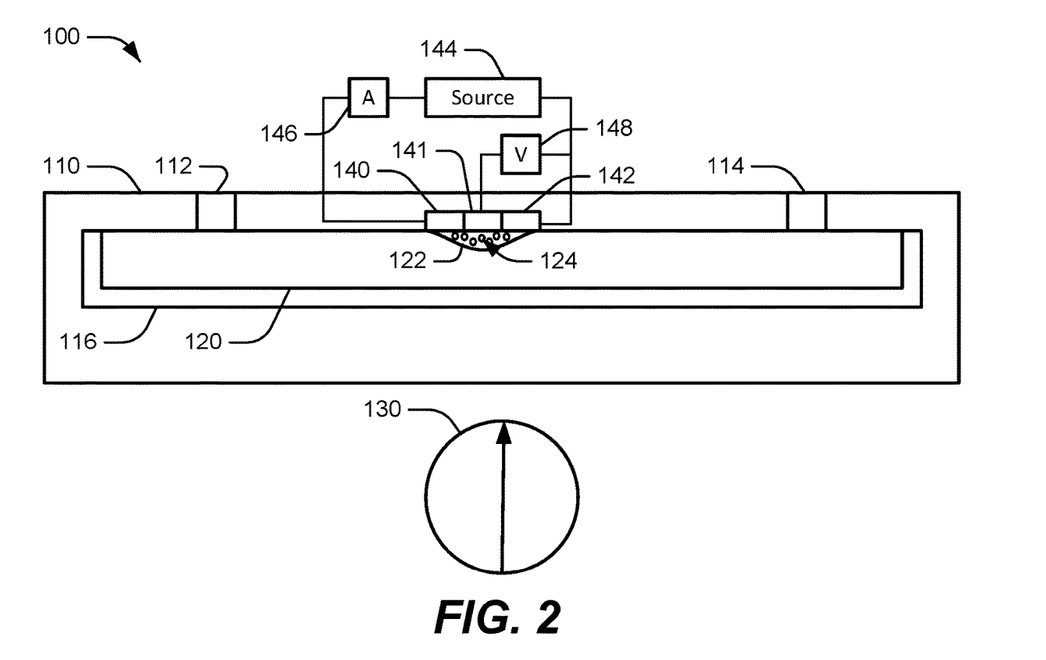
FIG. 2, is a diagram depicting the embodiment of the system for MSM alloy microcavity fluid sensing in a second pumping position.

Referring to FIG. 2, the position of the cavity 122 may be selectively changed. For example, the magnetic field source 130 may be controlled to continuously change the direction of the magnetic field (e.g., rotate the magnetic field), thereby selectively moving the cavity 122 from a first position adjacent to the inlet 112 to a second position adjacent to the electrodes 140-142. As the cavity 122 moves, it may retain the fluid 124, bringing the fluid 124 in contact with the electrodes 140-142.

While the fluid 124 is in contact with the electrodes 140-141, an electro-chemical analysis may be performed to determine the contents and/or a concentration of a substance within the fluid 124. For example, the voltage potential source 144 may apply a voltage potential across the working electrode 142 and the counter electrode 140. Due to the voltage potential, an electrical current may be created within the fluid 124 and may be measured at the ammeter 146. The measured electrical current may then be correlated to a particular substance or a concentration of a substance within the fluid 124. In order to account for possible voltage potential loss during to the generation of the current between the working electrode 142 and the counter electrode 140, a reference voltage may be measured at the voltmeter 148 via the reference electrode 141. The reference voltage may be used to correct and/or otherwise ensure the accuracy of the correlation.

Figure 3:
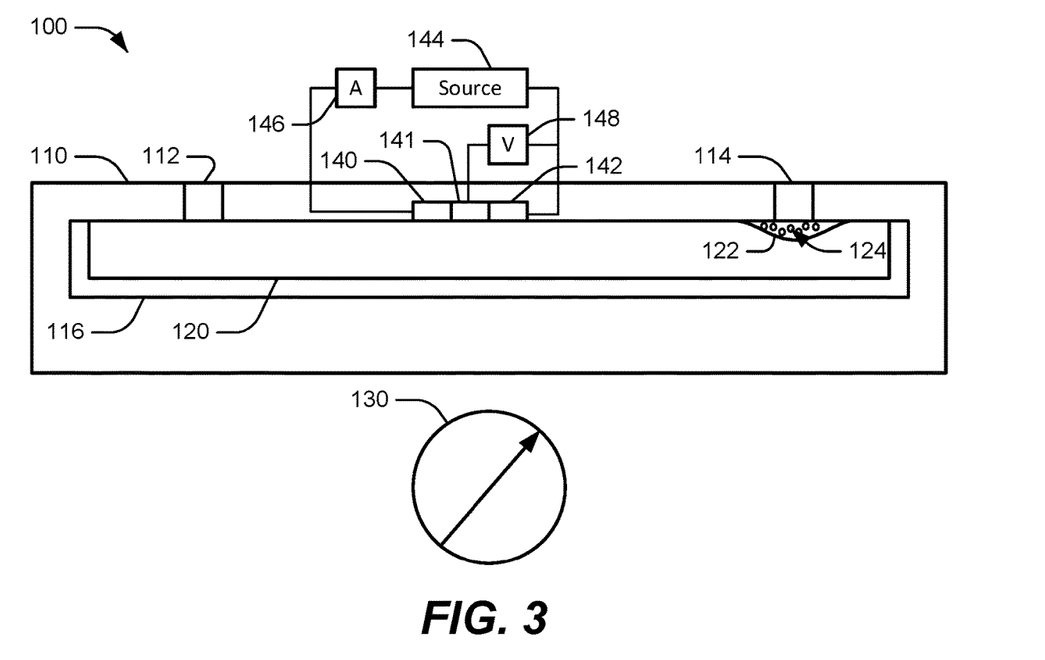
FIG. 3, is a diagram depicting the embodiment of the system for MSM alloy microcavity fluid sensing in a third pumping position.

Referring to FIG. 3, upon completion of the electro-chemical analysis, the magnetic field source 130 may resume or continue to change the direction of the magnetic field to selectively move the cavity 122 from the second position adjacent to the electrodes 140-142 to a third position adjacent to the outlet 114. The fluid 124 may then exit the cavity 122, passing through the outlet 114.

A benefit of the system 100 is that the system 100 enables electro-chemical analysis on fluids being transported through the system 100 in contrast to typical micropump systems that provide no analysis capabilities. Further, the volume of fluid sampled for every sample pulse within the system 100 is within the range of nano or micro liters in contrast to typical electro-chemical analysis systems which analyze volumes in the milliliter range. Thus, the system 100 may provide a smaller and/or more efficient method for electro-chemical analysis. Other benefits and advantages of the system 100 may be apparent to persons of ordinary skill in the relevant art having the benefit of this disclosure.

Figure 4:
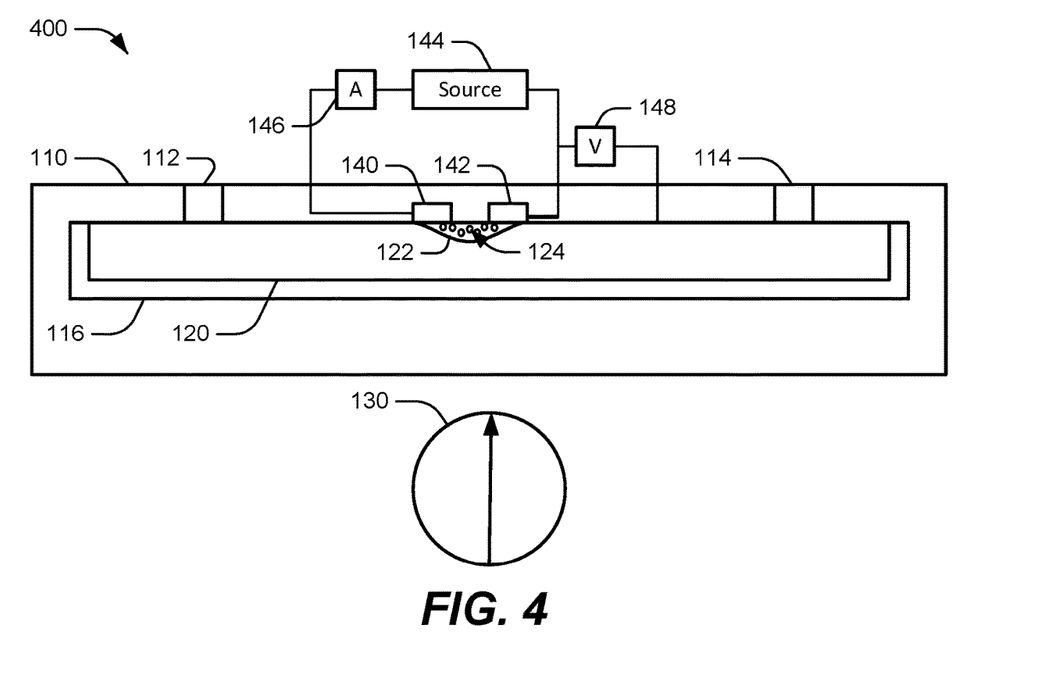
FIG. 4 is a diagram depicting an embodiment of a system for MSM alloy microcavity fluid sensing.

Referring to FIG. 4, an embodiment of a system 400 for MSM alloy microcavity fluid sensing is depicted. The system 400 differs from the system 100 in that the reference electrode 141 is omitted and the voltmeter 148 may be coupled between the working electrode 142 and the MSM alloy 120. In that way, the MSM alloy 120 may perform the same functions as the reference electrode 141.

For example, during operation, while the cavity 122 is adjacent to the electrodes 140, 142, the voltage potential source 144 may create a voltage potential between the counter electrode 140 and the working electrode 142. The voltage potential may create an electrical current that is measureable via the ammeter 146. In order to compensate for variability in the voltage potential between the counter electrode 140 and the working electrode 142, a voltage potential between the fluid 124 and the working electrode 142 may be measured via the MSM alloy 120.

Although, FIG. 4 depicts the MSM alloy 120 as performing the same functions as the reference electrode 141, in other embodiments any of the electrodes 140-142 may be replaced by the MSM alloy 120. To illustrate, two of the electrodes 140-142 may be combined with the MSM alloy 120 to form a group of three electrodes. The MSM alloy may function as either a reference electrode, a working electrode, or a counter electrode, depending of a particular application. For example, the voltage potential source 144 may be coupled in series between at least two of the group of three electrodes and the remaining electrode of the group of three electrodes may be configured to enable measurement of a common voltage during application of a voltage potential to the fluid.

A benefit of using the MSM alloy 120 to measure a reference voltage or to replace one of the electrodes 140, 142 is that the reference electrode 141, or another of the electrodes 140, 142 may be omitted, simplifying the system 400 as compared to the system 100. Other benefits and advantages of the system 400 may be apparent to persons of ordinary skill in the relevant are having the benefit of this disclosure.

Although FIGS. 1-4 depict the electrodes 140-142 as sequentially aligned parallel to a length of the channel 116 (e.g., parallel to the movement of the cavity 122), in some embodiments the electrodes 140-142 may be positioned in other configurations. For example, in some embodiments, the electrodes 140-142 may be positioned as perpendicularly aligned to the length of the channel in order to obtain better exposure to a cross-sectional volume of the fluid 124 at each of the electrodes 140-142 at the same time. Other positions for the electrodes 140-142 are also possible, depending on particular applications.

Figure 5:
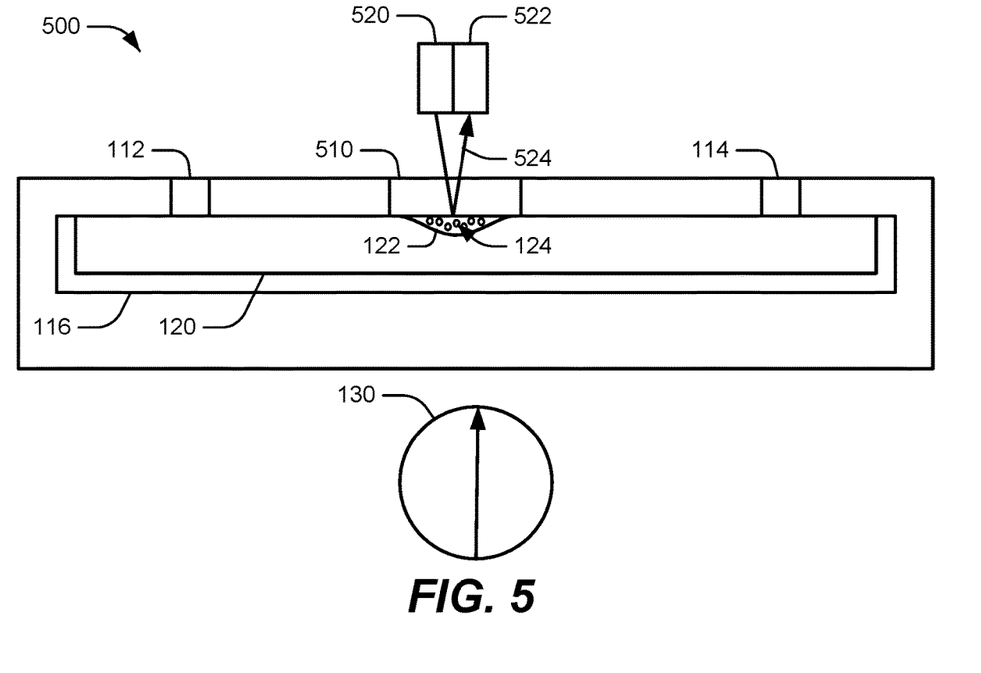
FIG. 5 is a diagram depicting an embodiment of a system for MSM alloy microcavity fluid sensing using a transparent window.

Referring to FIG. 5, an embodiment of a system 500 for MSM alloy microcavity fluid sensing is depicted. The system 500 may include a transparent window 510, a light source 520, and a detector 522.

The transparent window 510 may be positioned within the body 110 between the inlet 112 and the outlet 114 to enable light to enter and exit the cavity 122 when the cavity 122 is adjacent the transparent window 510. In some embodiments, the transparent window 510 is only transparent for a predetermined wavelength range or ranges.

The light source 520 may be directed at the transparent window 510. Light 524 from the light source may pass through the transparent window 510. The fluid 124 within the cavity 122 may reflect, transmit, or absorb the light, depending on the contents of the fluid 124, after which at least a portion of the light 524 may be received at a detector 522. In some embodiments, the light source 520 may be omitted and natural light may be used instead.

The detector 522 may directed at the transparent window 510. The detector may 522 be configured to detect particular cells and/or particles within the fluid 124. In some embodiments, the cells and/or particle may only be visible within some wavelength ranges. In those embodiments, the detector may detect light specific to those wavelength ranges.

During operation, the light source 520 may emit a beam of light that passes through the transparent window 510 and is at least partially reflected by the fluid 124 within the cavity 122 as a reflected light beam 524. The light 524 may render particular cells and/or particles visible. For example, the light 524 emitted from the source 520 may correspond to a predefined wavelength band or bands which render the cells and/or particles visible. The detector 522 may further be configured to count or otherwise determine a concentration of the cells and/or particles. Alternatively, in some embodiments, the detector may be configured to perform a spectro-analysis operation based on wavelengths reflected by the fluid 124 within the cavity 122 in order to determine the elemental makeup of the fluid 124. In either embodiment, the system 500 may enable a determination of the contents and/or concentration of the fluid 124.

Although described independently, it should be understood that the systems 100 and 400 may be joined with the system 500 such that both an electro-chemical analysis and an optical analysis may be made of the fluid 124 within the cavity 122. Other combinations of the embodiments described herein may be apparent to persons of ordinary skill in the relevant art having the benefit of this disclosure.

Figure 6:
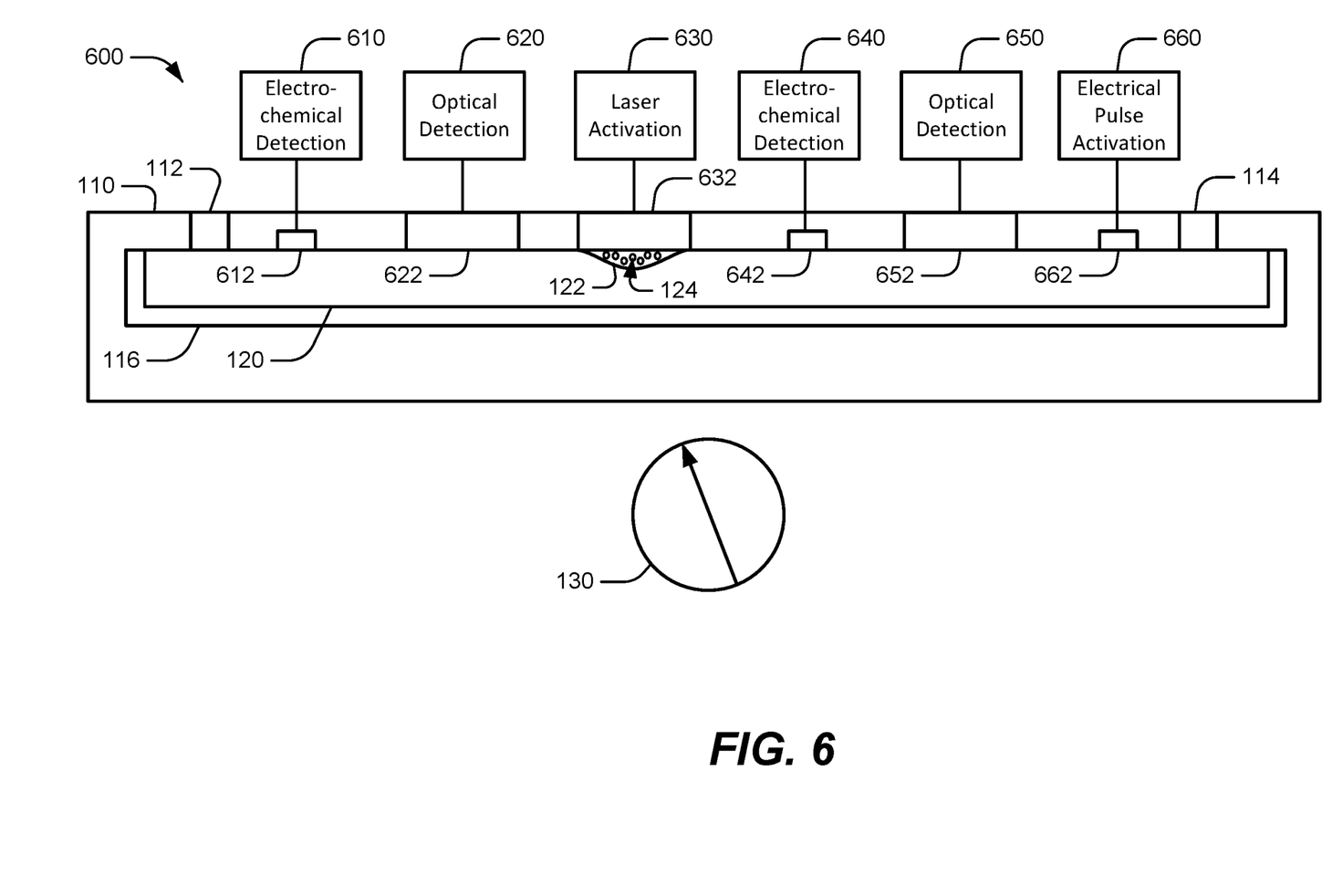
FIG. 6 is a diagram depicting an embodiment of a system for MSM alloy microcavity fluid sensing and activation.

Referring to FIG. 6, an embodiment of a system 600 for MSM alloy microcavity fluid sensing is depicted. The system 600 may include a series of multiple electrochemical detection systems 610, 640, multiple optical detection systems 620, 650, and multiple activation systems such as a laser activation system 630 and an electrical pulse activation system 660. The systems 610-660 may be positioned in any order along the channel 116 and in any combination. Additionally, in some embodiments, one or more of the systems 610-660 may be further repeated or omitted depending on a particular application of the system 600.

The electrochemical detection systems 610, 640 may include a first electrochemical detection system 610 and a second electrochemical detection system 640. The first electrochemical detection system 610 may be associated with at least one first electrode 612. The second electrochemical detection system 640 may be associated with at least one second electrode 642. Each of the electrochemical detection systems 610, 640, and the corresponding electrodes 612, 642, may operate as described with reference to the electrodes 140-142 and the corresponding circuitry described with reference to FIGS. 1-3 to enable the identification of and/or the concentration of a substance within the fluid 124. For example, the first electrode 612 may be included in part of a setup to measure electrical conductivity, chemical reactivity (e.g., via an oxidation-reduction process), or another type of chemical reaction associated with the fluid 124. Likewise, the second electrode 642 may be included in part of another setup to measure electrical conductivity, chemical reactivity (e.g., via an oxidation-reduction process), or another type of chemical reaction associated with the fluid 124. Although not shown in FIG. 6, additional electrodes may also be included as parts of other systems to detect electro-chemical properties associated with the fluid 124.

The optical detection systems 620, 650 may include a first optical detection system 620 and a second optical detection system 650. The first optical detection system 620 may be associated with a first transparent window 622. The second optical detection system 650 may be associated with a second transparent window 652. Each of the optical detection systems 620, 650, and the corresponding transparent windows 622, 652 may operate as described with reference to the 510, 520, 522 of FIG. 5 to enable the identification and quantification of particles within the fluid 124. Although not shown in FIG. 6, additional windows may also be included as parts of other systems to optically detect attributes and contents of the fluid 124.

The laser activation system 630 may use a laser to activate particles or substances within the fluid 124 via a transparent window 632. As used herein, to activate a particle or substance means to alter the particle by either transforming the particle or substance into another form or by otherwise destroying the particle or substance. During operation, one or both of the electrochemical detection systems 610, 640 and/or the optical detection systems 620 may identify particles or substances within the fluid 124 as the cavity 122 passed adjacent to the respective electrodes 612, 642 and/or transparent windows 622, 652. The cavity 122 may then be moved, using the magnetic field source 130 to place the fluid 124 in contact with the transparent window 632. The fluid 124 may then be subjected to the laser activation system 630 to activate particles or substances.

The electrical pulse activation system 660 may use electrical energy to activate particles or substances within the fluid 124 via an electrode 662. As with the laser activation system 630, activating a particle or substance means that the particle or substance is altered by either transforming the particle or substance into another form or by otherwise destroying the particle or substance.

As depicted in FIG. 6, after entering the cavity 122 via the inlet 112, the fluid 124 may be subjected to one or more of the systems, 610-660. The cavity 122 may be positioned adjacent to any of the systems and the fluid 124 need not pass through the system 600 sequentially. Further, the detection/activation systems 610-660 depicted in FIG. 6 are for example purposes only. Other embodiments may include any number of detection and/or activation systems and in any order. The system 600 may enable the identification and activation of particles within the system 600, whereas typical micropumps do not enable the identification and activation of particles and/or substances. Other benefits and advantages of the system 600 may be apparent to persons of ordinary skill in the relevant art having the benefit of this disclosure.

Figure 7:
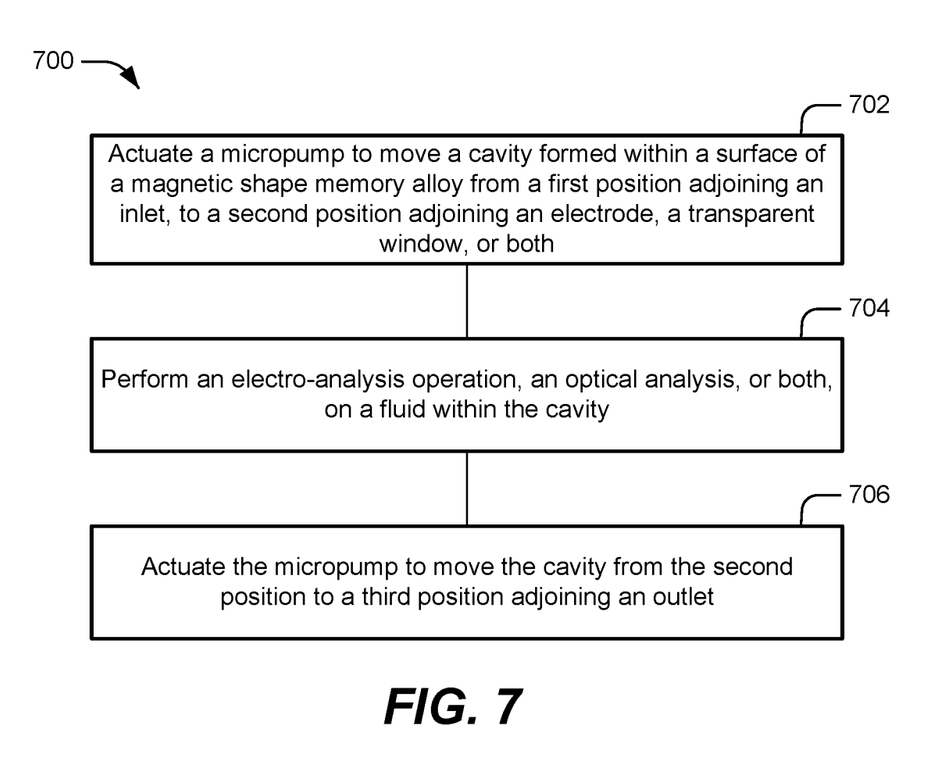
FIG. 7 is a flow diagram depicting an embodiment of a method for MSM alloy microcavity fluid sensing.

Referring to FIG. 7, an embodiment of a method 700 for MSM alloy microcavity fluid sensing is depicted. The method 700 may include actuating a micropump to move a cavity formed within a surface of a MSM alloy from a first position adjacent to an inlet, to a second position adjacent to an electrode, a transparent window, or both, at 702. For example, the systems 100, 400, and 500 may be actuated by rotating the magnetic field source 130 or by otherwise altering a magnetic field associated with the magnetic field source 130. By changing the magnetic field, the cavity 122 may be moved from a first position adjacent to the inlet 112 to a second position adjacent to the working electrode 142, the transparent window 510, or both in the case of a combined embodiment.

The method 700 may further include performing an electro-analysis operation, an optical analysis, or both, on a fluid within the cavity, at 704. For example, the cavity 122 may transport the fluid 124 from the inlet 112 to the second position. While in the second position, the working electrode 142 (and the additional electrodes 140, 141, if applicable) may be used to perform an electro-analysis operation on the fluid 124 as described herein. Likewise, in some embodiments, while in the second position, the light source 520 and detector 522 may be used to perform an optical analysis on the fluid 124 via the transparent window 510.

The method 700 may also include actuating the micropump to move the cavity from the second position to a third position adjacent to an outlet, at 706. For example, the system 100, 400, and 500 may be actuated by further rotating the magnetic field source 130 or by otherwise altering a magnetic field associated with the magnetic field source 130. By changing the magnetic field, the cavity 122 may be moved from the second position to a third position adjacent to the outlet 114. The fluid 124 may then dissipate through the outlet 114, having completed a pump cycle.

Although various embodiments have been shown and described, the present disclosure is not so limited and will be understood to include all such modifications, combinations, and variations as would be apparent to one skilled in the art.

What is claimed is:

1. A micropump comprising:
   a body;
   an inlet defined within the body;
   an outlet defined within the body;
   a channel connecting the inlet to the outlet;

a magnetic shape memory alloy positioned within the channel forming a barrier between the inlet and the outlet;

at least one electrode positioned along a surface of the channel within the body; and a cavity formed within a surface of the magnetic shape memory alloy due to a magnetic field, the cavity selectively moveable between a first position adjacent to the inlet, a second position adjacent to the electrode, and a third position adjacent to the outlet, by altering the magnetic field;

at least a second electrode, wherein the at least one electrode, the second electrode, and the magnetic shape memory alloy make up a group of three electrodes in contact with a fluid within the cavity when the cavity is in the second position; and a voltage source to enable application of a voltage potential to the fluid, wherein the voltage source is coupled in series between at least two of the group of three electrodes, and wherein the remaining electrode of the group of three electrodes is configured to enable measurement of a common voltage during application of the voltage potential.

2. The micropump of claim 1, further comprising:
a second electrode positioned along the surface of the channel, wherein the cavity is further selectively moveable to a fourth position adjacent the second electrode.

3. The micropump of claim 1, further comprising:
additional electrodes positioned along the surface of the channel, wherein the cavity is further selectively moveable to the additional positions.

4. The micropump of claim 1, further comprising:
a transparent window defined within the body and positioned adjacent the channel, wherein the cavity is selectively moveable to a fourth position adjacent the transparent window; and an optical detector directed toward the transparent window.

5. A micropump comprising:
a body;
an inlet defined within the body;
an outlet defined within the body;
a channel connecting the inlet to the outlet;
a magnetic shape memory alloy positioned within the channel forming a barrier between the inlet and the outlet;
at least one electrode positioned along a surface of the channel within the body;
a transparent window defined within the body and positioned adjacent the channel;
a light source directed toward the transparent window;
a detector directed toward the transparent window; and
a cavity formed within a surface of the magnetic shape memory alloy due to a magnetic field, the cavity selectively moveable between a first position adjacent to the inlet, a second position adjacent the transparent window, a third position adjacent to the at least one electrode, and a fourth position adjacent to the outlet, by altering the magnetic field.

6. The micropump of claim 5, wherein the transparent window is transparent to light within a predefined bandwidth.

7. The micropump of claim 5, wherein the light source is configured to generate light within a predefined bandwidth.

8. The micropump of claim 5, further comprising:
an activation device configured to activate at least one material identified via the transparent window, wherein the activation device includes at least one of a laser and an electrical pulse source.

* * * * *